United States Patent [19]

Ashby et al.

[11] 4,156,689

[45] May 29, 1979

[54] PURIFICATION OF HYDROSILANES AND SILOXANES

[75] Inventors: Bruce A. Ashby, Schenectady; Harry R. McEntee, Waterford, both of N.Y.

[73] Assignee: General Electric Company, Waterford, N.Y.

[21] Appl. No.: 877,054

[22] Filed: Feb. 13, 1978

[51] Int. Cl.$^2$ ............................................... C07F 7/20
[52] U.S. Cl. ............................................. 260/448.2 E
[58] Field of Search ................................. 260/448.2 E

[56] References Cited

U.S. PATENT DOCUMENTS

| 3,428,530 | 2/1969 | Fauche et al. | 260/448.2 E X |
| 3,440,264 | 4/1969 | McVannel | 260/448.2 E |
| 3,493,595 | 2/1970 | Strasser et al. | 260/448.2 E |
| 3,872,145 | 3/1975 | Breysse et al. | 260/448.2 E |

*Primary Examiner*—Paul F. Shaver
*Attorney, Agent, or Firm*—E. Philip Koltos; John L. Young; Philip L. Schlamp

[57] ABSTRACT

A process for the purification of hydrogen-containing silanes and siloxanes containing no phenyl substituent groups comprising contacting the silanes and siloxanes with an adsorbent bed formed from material selected from charcoal and molecular sieves and removing the purified silanes and siloxanes from the adsorbent bed. Through this procedure all the impurities which would poison the platinum catalyst are removed and as such the hydrosilanes and siloxanes will undergo SiH-olefin platinum-catalyzed reactions instantly and without difficulty.

24 Claims, No Drawings

PURIFICATION OF HYDROSILANES AND SILOXANES

BACKGROUND OF THE INVENTION

The present invention relates to a process for the purification of hydrogen-containing silanes and siloxanes and more particularly the present invention relates to a process for the purification of hydrogen-containing silanes and hydrogen-containing siloxanes having no phenyl substituent groups so as to remove from said silanes and siloxanes all impurities which would poison a platinum catalyst.

The SiH-olefin platinum-catalyzed reactions are well known. There is also produced a room temperature vulcanizable silicone rubber product which is formed through an SiH-olefin, platinum-catalyzed reaction. Such product generally comprises a hydride polysiloxane which is normally packaged in a separate package and a second component which is a mixture of a vinyl-containing polysiloxane, filler and a platinum catalyst. When the two components are mixed, the hydrogen of the hydrogen-containing siloxane in the presence of the platinum catalyst adds to the olefinic group in the vinyl-containing polysiloxane to cross-link and cure the composition at room temperature to a silicone elastomer. As can be appreciated, it is vital in such processes and compositions that the platinum catalyst not be poisoned.

Accordingly, if the hydride siloxane or the vinyl polysiloxane component contains impurities which will poison the platinum catalyst, then the composition will not cure when the two components are mixed together. There also can be present impurities in the composition which will retard or partially poison the platinum catalyst, thus requiring additional amounts of platinum catalyst to carry out the reaction, thus increasing the expense of the product. It has been found that normally such impurities come into the product with the hydrogen-containing polysiloxane. At any rate, it is desirable to obtain the hydrogen-containing polysiloxane in as pure a form as possible and without containing impurities which can poison the platinum catalyst since if that is the case, then the SiH-olefin reaction will proceed without difficulty and with the use of only a very small amount of the platinum catalyst. Normally, such hydrogen-containing polysiloxanes are obtained by hydrolyzing in water, the appropriate dichlorosilane with the appropriate amount of hydrochlorosilane chain-stoppers to obtain a low molecular weight linear polysiloxane polymer with the appropriate hydrogen substitution. Such a polymer can then be utilized as a cross-linking agent in SiH-olefin, platinum-catalyzed compositions to produce room temperature vulcanizable silicone rubber compositions. Accordingly, then a hydrogen-containing polysiloxane utilized in such SiH-olefin reactions must be as pure as possible and contain as little as possible of impurities as is the case with the hydrogen-containing chlorosilane that is produced therefrom. Accordingly, it is desired to have the appropriate hydrogen-containing chlorosilane as pure as possible and as free as possible of impurities. It should be noted that it is desired that hydrogen containing chlorosilanes in another respect be as free of impurities that poison platinum catalysts since such hydrogen-containing silanes, for instance methyldichlorosilane, are utilized to produce many intermediates which are further reacted to produce silicone elastomers and silicone fluids. For instance, dimethylhydrogenchlorosilane is reacted with vinyl acetonitrile in the presence of a platinum catalyst to produce the corresponding nitrile chlorosilane which chlorosilane is then hydrolyzed selectively or otherwise to produce the appropriate nitrile substituted silicone fluid and in which fluid the nitrile group can be further hydrolyzed into a carboxy group. Such materials can find use, for instance, as surfactants or as intermediates for producing polysiloxane-polyether copolymers which are very useful as polyurethane foam surfactants.

Another reaction which is important with a hydrogen-containing polysiloxane is the reaction of hydrogen-containing polysiloxane low molecular weight fluid with alpha-methylstyrene or with hexene to produce in the presence of a platinum catalyst the appropriate addition product. Again such substituted polysiloxane materials are useful as silicone paintable water-repellent fluids.

A more important and prominent process of chlorosilanes is the reaction of methyldichlorosilane with 3,3,3-trifluoropropene to produce 3,3,3-trifluoropropylmethyldichlorosilane. This reaction is also carried out in the presence of a platinum catalyst. Such dichlorosilane addition products after they are formed are hydrolyzed in water to produce a mixture of low molecular weight linear polysiloxanes, and a mixture of cyclosiloxanes in which the predominate species in the cyclosiloxanes is the cyclictrisiloxanes and cyclotetrasiloxanes.

By adding an alkali metal hydroxide catalyst to the hydrolyzate, such as, potassium hydroxide, in the appropriate amounts and cracking the hydrolyzate at elevated temperatures, that is, temperatures above 150° C., there can be preferentially distilled overhead cyclotrisiloxanes in large yields. Such cyclotrisiloxanes may then be taken and there may be added to them a small amount of alkali metal hydroxide catalyst such as, potassium hydroxide at a concentration of anywhere from 10 to 500 parts per million and there is also added to the mixture the necessary amounts of low molecular weight linear polysiloxane chain-stopper such as, for instance, hexylmethyldisiloxane. The resulting mixture is heated at elevated temperatures, that is, temperatures above 150° C. to convert the cyclotrisiloxane to a linear polysiloxane polymer having 3,3,3-trifluoropropyl substituent groups. Such a polymer with the appropriate amount of filler and peroxide curing catalyst can be cured at elevated temperatures to form a silicone elastomer with excellent solvent resistance. Accordingly, as can be envisioned, the reaction of the methyldichlorosilane with 3,3,3-trifluoropropene in the presence of a platinum catalyst is a very important step in the carrying out of the preparation of such solvent resistant silicone elastomers. However, it has been found that the reaction at times would not initiate, even after prolonged waiting or contact between the methyldichlorosilane and the 3,3,3-trifluoropropene. It was found on occasions that the reaction would not initiate even with heating of the mixture above room temperature and also even with other steps being taken to initiate the reaction. Such failures of the reaction to initiate many times resulted in the loss of materials, that is, the materials have to be discarded and new materials had to be used, and of course there was the wasted time and labor. This would unduly increase the cost of the overall process. It was found that at times, that after the reaction had failed to initiate, the reaction could be initiated by the addition of additional platinum catalyst. However, one difficulty with this addition was to increase the cost that was imputed to the process. Further, many times there would be a large amount of olefin present in the reaction mixture because of the continuous feeding of olefin to the hydrogen-containing siloxane in the reaction vessel as is normal during such reactions, and as a result the reaction might initiate suddenly and many times violently, thus creating a safety hazard. At any rate, it was determined that the reason for this inability to initiate the reaction, in some cases, was due to the presence of impurities in the hydrogen-containing polysiloxane from the process by which it was made which impurities were not removed by the distillation procedure utilized to purify the hydrogen-containing silanes. Hydrogensilanes are formed in the basic reaction of methylchloride with silicon metal in the presence of a copper catalyst at elevated temperatures, that is, temperatures in the neighborhood of 300° C., or above where there is formed a host of methylchlorosilanes and hydrogen-containing silanes. The specific chlorosilanes are then separated from the mixture by fractional distillation. It has been found that by such fractional distillation and even by repeated distillation purification procedures that in some cases the platinum-poisoning impurity was not removed from the hydrogen-containing silane.

Accordingly, it was highly desirable to find the process to purify such hydrogen-containing silanes and to remove the impurities which would poison the platinum catalyst. It should be noted that at this time it is not known for certain what these impurities that poison the platinum catalyst are. It is felt that possibly the impurity is sulfur since 5 parts per million of sulfur will poison 100 parts per million of platinum. However, sulfur is very hard to analyze for in hydrogen-containing silanes and as such, at this time, what the impurities are that would poison the platinum catalyst and hydrogen-containing silanes is not known for certain. However, at any rate, various purification processes were tried to remove such impurities from the hydrogen-containing silanes and siloxanes, all of which met with failure. Such purification processes were basically distillation procedures. There should also be noted the process of the patent application of Harry R. McEntee, entitled "Process for Removing Biphenyls from Chlorosilanes", Ser. No. 828,367, filed on Aug. 29, 1977. This patent application deals with the removal of chlorinated biphenyls from streams of silane and siloxanes containing aromatic substitution, by contacting the streams of silanes and siloxanes with an adsorbent bed of molecular sieves and more preferably an adsorbent bed made of activated carbon so as to absorb the biphenyl impurities into the adsorbent bed. However, prior to the present time, such a process had never been tried on hydrogen-containing silanes and siloxanes for removing impurities therefrom which impurities would poison the platinum catalyst in SiH-olefin addition reactions.

Accordingly, it is one object of the present invention to provide for a process for removing impurities which would poison a platinum catalyst from a stream of hydrogen-containing silanes and hydrogen-containing siloxanes.

An additional object of the present invention is to remove impurities from hydrogen-containing silanes and hydrogen-containing siloxanes which impurities would poison the platinum catalyst by contacting the hydrogen-containing silanes and hydrogen-containing siloxanes with an adsorbent bed constructed of molecular sieves.

It is still an additional object of the present invention to provide for a process for removing impurities from hydrogen-containing silanes and hydrogen-containing siloxanes having no aromatic substitution, which impurities would poison the platinum catalyst in an SiH-olefin platinum-catalyzed reaction.

It is yet an additional object of the present invention to provide for a process for removing impurities from hydrogen-containing silanes and hydrogen-containing siloxanes having no aromatic substitution by contacting the hydrogen-containing silanes and hydrogen-containing siloxanes with an adsorbent bed constructed from charcoal wherein the impurities are such that they would poison a platinum catalyst in an SiH-olefin, platinum-catalyzed reaction.

These and other objects of the present invention are accomplished by means of the disclosure set forth hereinbelow.

SUMMARY OF THE INVENTION

There is provided by the present invention and in accordance with the above objects a process for the purification of hydrogen-containing silanes and siloxanes comprising (1) contacting the hydrogen-containing silanes and siloxanes having no aromatic substituent groups with an adsorbent bed comprising adsorbent materials selected from the class consisting of charcoal and molecular sieves so as to remove therefrom all impurities which would poison a platinum catalyst and (2) removing the purified silanes and siloxanes from the adsorbent bed. Preferably, the first volume of hydrogen-containing silanes and siloxanes is used to wet the adsorbent bed until the adsorbent material is wet. A period of time is allowed to pass until the adsorbent material, which upon being wetted gives off heat, reaches room temperature. At that time the first volume of hydrogen-containing silane material is segregated and there is then continuously passed into the adsorbent bed the hydrogen-containing silanes and siloxanes so as to remove the impurities therefrom and remove from the adsorbent bed the purified hydrogen-containing silanes and siloxanes. The first segregated volume of hydrogen-containing silanes or siloxanes which was used to wet the adsorbent bed if it will not initiate or take part in the SiH-olefin addition reaction may then be recycled through the adsorbent bed whereupon with additional purification it will be able to take part in SiH-olefin reactions without any difficulty. When the adsorbent bed has been saturated with the impurities then the adsorbent material can then be simply discarded and a stream of silanes and siloxanes continuously passed onto a second bed filled with new adsorbent material wherein the adsorbent material that has been previously wetted and the first volume of fluid segregated as discussed previously.

Accordingly, in this manner the purification of the hydrogen-containing silanes and siloxanes can be carried out in a continuous manner so as to remove the platinum-poisoning impurities therefrom as rapidly and as quickly as possible. Although charcoal and activated carbon, a specific form of charcoal, can be utilized as the adsorbent materials, by and large the most preferred adsorbent material in the process of the instant case is molecular sieves.

DESCRIPTION OF THE PREFERRED EMBODIMENT

The McEntee process referred to previously with respect to the McEntee patent application is a general process for removing biphenyls and more specifically chlorinated biphenyls from streams of silanes and siloxanes. Such a process comprises passing streams of silanes and siloxanes through adsorbent beds of activated carbon or molecular sieves to remove the biphenyls from the streams of silanes and siloxanes. Such biphenyls become present in the streams of silanes and siloxanes as the result of the process for forming phenyl-containing silanes and siloxanes. Basically, the process for forming phenyl-containing silanes and siloxanes is reacting chlorobenzene with silicon metal in the presence of a copper catalyst at elevated temperatures. As a result of such a process the desired phenylchlorosilanes are formed. However, as by-products of the process there are formed in minute quantities chlorinated biphenyls. A substantial number of such chlorinated biphenyls are removed by distillation purification techniques. However, a certain amount of chlorinated biphenyls are not so removed. Accordingly, it was McEntee's invention of the foregoing patent application of taking such phenyl-containing silanes and passing them through adsorbent bed of molecular sieves or activated carbon so as to adsorb the chlorinated biphenyls on the adsorbent bed of activated carbon, thus purifying the stream. Although it was appreciated at the time of the patent application of McEntee that other impurities could be taken out of the stream of phenyl-containing silanes and phenyl-containing siloxanes, it was not appreciated that such a process could be applied to non-phenyl containing streams of silanes and siloxanes.

Accordingly, it was not known what impurities there were, for instance, in streams of non-phenyl-containing silanes and siloxanes or how those impurities could be removed. To state the matter briefly, there was no research carried out as to the removal of impurities from streams other than streams of phenyl-containing silanes and siloxanes so as to remove impurities therefrom utilizing the adsorption process with molecular sieves or activated carbon. The reason for this is that the investigation of McEntee centered around phenyl-containing streams of silanes and siloxanes since such streams were the only ones that contained in them chlorinated biphenyls. Accordingly, McEntee in his patent application did not investigate the purification of any other stream of silanes and siloxanes as to what impurities could be taken out from them and in fact did not at that time appreciate if an adsorption process could be utilized in the purification of streams of silanes and siloxanes other than by the adsorption of biphenyls.

Hydrogen-containing silanes are produced by a very basic process. The hydrogen-containing siloxanes are produced from hydrogen-containing chlorosilanes and are as pure as the hydrogen-containing chlorosilanes from which they are produced. Hydrogen-containing chlorosilanes are by-products of the basic process in which methylchloride is reacted with silicon metal in the presence of a copper catalyst at elevated temperatures, that is, temperatures in the neighborhood of 300° C. When the foregoing reaction is carried out, there results many types of basic chlorosilane products and by-products. The basic silane products and by-products are as follows:

MeH$_2$SiCl
Me$_4$Si
HSiCl$_3$
Me$_2$HSiCl
MeHSiCl$_2$
Me$_3$SiCl
MeSiCl$_3$
Me$_2$SiCl$_2$

In such a process there is also produced a certain amount of hydrocarbon by-products, that is, organic, non-silicone compounds. These by-product compounds are as follows:

CH$_3$CH(CH$_3$)CH$_2$CH$_3$
CH$_3$CH$_2$C(CH$_3$)CH$_2$
CH$_3$CHC(CH$_3$)CH$_3$
CH$_3$CH$_2$C(CH$_3$)$_2$CH$_3$
CH$_3$CH(CH$_3$)CH$_2$CH$_2$CH$_3$
CH$_3$CH(CH$_3$)CH(CH$_3$)CH$_3$
CH$_3$CH$_2$CH(CH$_3$)CH$_2$CH$_3$

The silane products are, of course, the ones that the silicone manufacturers are interested in. To obtain a particular chlorosilane in the highest yield the crude liquid that comes from the foregoing process for producing chlorosilanes is taken and there is fractionally distilled from it the various chlorosilanes, methyldichlorosilane being the preferred chlorosilane for the reaction with 3,3,3-trifluoropropene for producing solvent resistant silicone elastomers. Other desired fractions for utilization in SiH-olefin platinum-catalyzed reactions are trichlorosilane, dimethylchlorosilane and dichlorosilane. At any rate it has been found that when such streams of chlorosilanes have been purified by distillation after the initial fractional distillation, that after such distillation purification techniques that such hydrochlorosilanes contain in them some impurities which prevent them from reacting in an SiH-olefin platinum-catalyzed reaction. It is postulated that the reason for lack of reaction is the poisoning of the platinum catalyst by some impurity in the hydrochlorosilane. What the impurities are it is not known. It is postulated that possibly the impurity is sulfur since it is known that sulfur will poison a platinum catalyst very readily. The reason the sulfur impurity has not been verified by analytical techniques is that it is very difficult to analyze for sulfur in hydrosilanes by known analytical methods. At any rate various procedures have been tried to analyze for possible impurities that are present in the hydrochlorosilane stream that would poison the platinum catalyst. At this time the determinations have not been conclusive except for the above-mentioned postulations.

It can be appreciated that the comments above are pure theory which have not as yet been substantiated by experimental evidence. It had been found that whatever these impurities are that poison the platinum catalyst, they can be removed by passing the stream of hydrochlorosilanes or siloxanes in contact with an adsorbent bed where the adsorbent bed is formed or can be formed alternatively from charcoal, or molecular sieves. One form of charcoal is activated carbon which was very desirable in the foregoing McEntee process discussed in the McEntee patent application. However, activated carbon and particularly charcoal in general while acting as a very good adsorbent material for the chlorinated biphenyls of the previous McEntee patent application do not perform as well as an adsorbent bed for the impurities in the streams of hydrogen-containing silanes and hydrogen-containing siloxanes.

It has been found that the preferred adsorbent material for the impurities that may be present in streams of hydrogen-containing silanes and hydrogen containing siloxanes is molecular sieves. It should be noted from hereon that there shall be only reference made to hydrogen-containing silanes in the description of the process, since such silanes are most likely to be exposed to the process of the instant case. Although hydrogen-containing siloxanes may also be purified by the instant process, it is easier to subject, hydrogen-containing silanes before they are polymerized to siloxanes, to the instant process since they can be more readily used as intermediates. It is also true hydrogen-containing silanes can be utilized as intermediates in the production of the specified chlorosilanes in an SiH-olefin platinum-catalyzed reaction to produce fluorosilicone elastomers after having been purified by the instant process. Thus, siloxanes can be purified by the instant process but silanes are the ones most likely to be purified by the instant process so, accordingly, the reference in the instant specification hereinafter will be to hydrogen-containing silanes or chlorosilanes with the understanding that the process can also be applied to siloxanes.

It can also be understood that in the instant process the hydrogen-containing silanes may be purified in the form of a liquid or a vapor. It is preferred that the hydrogen-containing silanes be purified in the form of a liquid since more impurities are adsorbed, the equipment size can be made smaller, and the streams of chlorosilanes are easier to handle. With respect to activated carbon or charcoal any charcoal or activated carbon can be used having an average particle size ranging from ¼ inch to 3 to 4 microns. It is appreciated that the smaller the particle size of the charcoal or activated carbon that the more efficient the adsorption, since the larger the surface area of the charcoal or activated carbon. However, the most preferred adsorbent material is molecular sieves. Molecular sieves are both synthetic and naturally occurring alumina silicate materials which will adsorb various types of impurities from various types of materials. However, it has been found in the instant invention that molecular sieves are very efficient in adsorbing the impurities that poison a platinum catalyst from streams of chlorosilanes. Again, the molecular sieves may have a size in the range from ⅛ inch in average particle size to 100 to 125 microns average particle size. It is preferred that the molecular sieves have the finer particle size when utilized in adsorbent beds in the instant invention since the finer the particle size of the molecular sieves, the larger the surface area of the adsorbent bed and the more efficient the adsorption of impurities from the stream of chlorosilanes. However, where efficiency is not a prime factor, any particle size for the molecular sieves can be utilized. If efficiency is a prime requirement then it may be desirable that the molecular sieves not have as fine a particle size as possible, since it is desirable to obtain a good flow rate of the chlorosilanes through the adsorbent bed. It can be appreciated that the finer the particle size of the molecular sieves the higher the pressure that will be needed to push a certain flow rate of hydrosilanes through the adsorbent bed. By simply passing the stream of hydrogen-containing silanes through the adsorbent bed, the undesirable platinum poisoning impurities are removed therefrom in sufficient quantities such that the hydrogen-containing silanes can immediately be initiated into an addition reaction with olefinic compounds in the presence of a platinum catalyst. As a matter of fact, the test of proper purification of hydrogen-containing silanes in accordance with the instant invention is that the purified material that is obtained from the adsorbent bed will immediately enter into an SiH-olefin addition reaction with minimal quantities of platinum catalyst being present. The commercial names of such molecular sieves and charcoal are many. Examples of such are as follows, as well as an example of their particle size:

Activated Carbon: Pittsburgh BL, minus 325 mesh, manufactured by Calgon Corp.

Activated Carbon: Pittsburgh CAL, 12 × 40 mesh, manufactured by Calgon Corp.

Activated Coconut Charcoal: Pittsburgh PCB, 4 × 10 mesh, manufactured by Calgon Corp.

13 × molecular sieves,: 8 × 12 mesh, manufactured by W. R. Grace Co. and by Union Carbide Corp.

10 × molecular sieves,: 45 × 60 mesh, manufactured by W. R. Grace Co. and by Union Carbide Corp.

The adsorbent bed is most desirably incorporated in the form of a column through which the chlorosilane can be pumped. An example of an adsorbent bed in a column, for instance is one in which the adsorbent bed has a cross-sectional area of 1,227 sq. feet, has about 460 lbs. of Union Carbide 13× molecular sieves, the volume of a bed being for instance, 10 cubic feet and a bed height of 8.5 feet. The above data on a typical adsorbent bed is not given for any purpose of limiting the instant invention, it is given for the purpose of illustrating a typical bed of adsorbent molecular sieves that can be utilized within the scope of the instant invention. The chlorosilanes are then simply pumped through the adsorbent bed in accordance with the information that will be given below to obtain their purification. Generally, the adsorbent process is preferably carried out anywhere at a temperature of 0° to 35° C. It is undesirable to carry out the adsorbent process at a temperature of the adsorbent bed above 35° C., since the adsorption is not very efficient at that point. Further, the chlorosilanes tend to vaporize at temperatures above that level. With respect to the 0° C. lower limit, the only reason the lower limit appears is that it is difficult to refrigerate an adsorbent bed below the 0° level. However, temperatures below 0° C. for the adsorbent bed could be utilized to carry out the adsorption process therewith. Preferably, the adsorption process is carried out at room temperature since this does not require refrigeration and the adsorption process has been found to be carried out efficiently at room temperature. It should be pointed out that before the stream of hydrogen-containing silanes is passed through the adsorbent bed, it is desirable they be purified as much as possible by distillation so that the impurities easily separated by distillation are not present in the chlorosilane stream and thus become adsorbed on the adsorbent bed, saturating it with impurities, thus, shortening its useful life. Accordingly, it is highly desirable that the chlorosilane stream before it is passed through the adsorbent bed, be purified by distillation once, twice or more times before it is subjected to the instant process. It has been found in practice that a doubly distilled stream of methyldichlorosilane can be subjected to the instant process with maximum efficiency. The residence time of the stream of chlorosilanes in the adsorbent bed will vary with practice. It has been found that a residence time of as little as 0.5 hours in the adsorbent bed will remove a substantial amount of platinum poisoning impurities while a maximum time of 10 hours will completely purify the stream of chlorosilanes.

More preferably, there is utilized a residence time in the adsorbent bed for the stream of chlorosilanes of anywhere from 1 to 4 hours. It has been found that in most adsorbent beds such as the typical adsorbent bed discussed previously that the appropriate amount of impurities are taken out of the stream of chlorosilanes in the above time to leave behind a purified chlorosilane which will immediately enter into an SiH-olefin platinum-catalyzed reaction. It should be noted that there is no problem with having the residence time being longer than 10 hours in the adsorbent bed. The only problem with such longer residence time is that it is uneconomical in the terms of processing chlorosilanes in a manufacturing silicone plant.

Accordingly, the stream of chlorosilanes may be pumped through an adsorbent bed such as the typical one discussed previously at a range varying anywhere from 5 to 800 lbs. of chlorosilanes per hour, per sq. foot of adsorbent bed cross-sectional area, and more preferably from 100 to 500 lbs. per hour, per sq. ft. of adsorbent bed cross-sectional area. The general range given above for pumping the stream of chlorosilanes in the cross-sectional area of adsorbent bed is meant to be as broad as possible to cover all possible eventualities for pumping chlorosilanes in the adsorbent bed. With respect to the minimum level, it would be very uneconomical to pump through chlorosilanes through an adsorbent bed at less than 5 lbs. per hour. With respect to the maximum level of 800 lbs. per hour of sq. ft. of cross-sectional area of adsorbent bed, it can be appreciated that columns could be constructed of such a size to accommodate higher flow rates if this was thought to be necessary. Accordingly, the general range that has been given is to cover within its scope the practical applications in a silicone plant for the purification of chlorosilanes. The preferred range is to cover the most practical conditions for the purification of chlorosilanes in silicone manufacturing plants. Accordingly, with the above information, a column can be constructed for the purification of chlorosilanes so as to remove impurities therefrom so such chlorosilanes can easily enter into an SiH-olefin platinum catalyzed reaction. In addition, it should be noted that molecular sieves are very efficient adsorbents for platinum poisoning impurities. Accordingly, it is generally desired that there be utilized a molecular sieve material in said adsorbing bed such that at least 75 pounds of chlorosilanes or siloxanes are purified to the appropriate level by removing platinum poisoning impurities per pound of adsorbent material before the adsorbent material has to be replaced. More preferably, it is desired that there be purified from 75 to 500 pounds of chlorosilanes and streams of chlorosilanes per pound of adsorbent material, such that said chlorosilanes can easily enter into an SiH-olefin platinum-catalyzed reaction before said adsorbent material has to be replaced. As has been mentioned previously, molecular sieves being a very efficient adsorbent material in the process of the instant case can meet the above requirements. The amount of stream of chlorosilanes that can be processed by a particular adsorbent material and purified by a given quantity of adsorbent material is important in the economics of the instant process. Thus, the higher the amount of chlorosilanes that can be purified by a given pound of adsorbent material in accordance with the instant process, the less expensive the instant process is.

It has been found that with molecular sieves at least 75 pounds of chlorosilanes can be purified per pound of adsorbent material before the adsorbent material has to be rejuvenated or replaced. In the most preferred embodiment, the adsorbent material is simply discarded after it is saturated with impurities. Then the chlorosilanes are simply processed through a new bed of molecular sieves in accordance with the instant process. Accordingly, because of their economy, molecular sieves are highly desirable to form the adsorbent bed in the instant process.

For the above reasons of economy and efficiency, it is also desirable that the instant purification process be carried out in a continuous manner. Accordingly, the best fashion to carry out the instant process is to add a first volume of chlorosilanes to a bed of adsorbent material, thoroughly wetting the adsorbent material. It has been found that when a first volume of chlorosilanes wets the adsorbent material that there is liberated heat and that the first volume of fluid is not purified in all cases so that it can easily enter into an SiH-olefin platinum-catalyzed reaction. If the first volume of chlorosilanes is purified then it can be utilized as such and passed on into the main stream of the other processes. If it is not so purified, then it is simply segregated. After the adsorbent bed has reached room temperature, additional chlorosilanes are processed through the adsorbent bed and purified as is desired. The segregated first volume of material which in some cases may not pass the SiH-olefin platinum-catalyzed addition test, may then be recycled through the adsorbent bed and entered into the plant main stream as is desired. It should be noted that the desired adsorbent bed is allowed to reach room temperature after it has been first wetted since it has been found that the adsorption process of the instant case is carried out more efficiently with the adsorbent bed at room temperature or generally in the temperature range of 0° to 35° C. Accordingly, after the first volume of material has been segregated, if necessary, then the chlorosilanes can be continuously processed through the adsorbent bed to continuously remove impurities therefrom.

A second bed of adsorbent material may then be prepared and pre-wetted with chlorosilanes such that it is ready for use. When the first bed of adsorbent material becomes saturated with impurities such that it can no longer remove the desired amount of impurities from the stream of chlorosilanes, then the stream can be switched on to the second bed of adsorbent material in a continuous manner and the platinum poisoning impurities can be continuously removed from the stream of chlorosilanes.

The first bed of adsorbent materials saturated with impurities may then be discarded and new adsorbent materials inserted into the column. This column can then be again pre-wetted with a volume of chlorosilanes and after it has reached room temperature it will be ready for use to continuously adsorb impurities from the stream of chlorosilanes after the second adsorbent bed has become saturated with impurities.

By such a means there can always be a continuous processing of chlorosilanes through an adsorbent bed to remove the platinum poisoning impurities. It should be noted, as stated previously, that the first volume of chlorosilanes that is utilized to wet the adsorbent bed may not always be purified sufficiently to enter an SiH-olefin addition reaction immediately. Accordingly, such a first volume of material may be recycled through the adsorbent bed if this is necessary. In accordance with the instant invention, there is provided a process for continuously removing platinum poisoning impurities from streams of chlorosilanes and siloxanes, and more specifically from streams of hydrogen-containing silanes and hydrogen-containing siloxanes containing no aromatic substituent groups.

It can be appreciated that the above process can also be carried out in removing platinum poisoning impurities from streams of olefins and specifically organic olefins or polysiloxanes having olefin substituent groups. The process would be the same; the only difference would be that they would be olefinic compounds subjected to the process.

In accordance with the instant process there is envisioned the removing of platinum poisoning impurities by passing the stream of olefinic compounds, specifically, organic olefins, through an adsorbent bed formed from charcoal and most preferably from molecular sieves since it has been found, as stated previously, that molecular sieves are the most efficient adsorbing ingredient as far as adsorbing platinum poisoning impurities from streams of silanes and siloxanes.

The process conditions and procedures for purification of olefins would be the same as that given previously for the stream of chlorosilanes and siloxanes.

It should be noted that the impurities that have been found in hydrosilanes or chlorosilanes do not appear to be present in organic olefinic compounds. However, if such impurities were present in olefinic organic compounds, then the process of the instant case could be applied to purify such materials so as to remove platinum-poisoning impurities therefrom.

It should be noted that the instant process can be utilized to purify chlorosilanes if such chlorosilanes are to be used to enter or take part in an SiH-olefin reaction with any type of platinum catalyst.

Examples of platinum catalysts that can be utilized in such SiH-olefin platinum catalyzed reactions are many.

Many types of platinum compounds for this SiH-olefin addition reaction are known and such platinum catalysts may be used also for the reaction of the present case. The preferred platinum catalysts especially when optical clarity is required are those platinum compound catalysts which are soluble in the present reaction mixture. The platinum compound can be selected from those having the formula $(PtCl_2.Olefin)_2$ and $H(PtCl_3.Olefin)$ as described in U.S. Pat. No. 3,159,601, Ashby. The olefin shown in the previous two formulas can be almost any type of olefin but is preferably an alkenylene having from 2 to 8 carbon atoms, a cycloalkenylene having from 5 to 7 carbon atoms or styrene. Specific olefins utilizable in the above formulas are ethylene, propylene, the various isomers of butylene, octylene, cyclopentene, cyclohexene, cycloheptene, etc.

A further platinum-containing material usable in the composition of the present invention is the platinum chloride cyclopropane complex $(PtCl_2.C_3H_6)_2$ described in U.S. Pat. No. 3,159,662, Ashby. Still, further, the patent containing material can be a complex formed from chloroplatinic acid with up to 2 moles per gram of platinum of a member selected from the class consisting of alcohols, ethers, aldehydes and mixtures of the above as described in U.S. Pat. No. 3,220,971, Lamoreaux.

All the patents and patent applications mentioned in this present specification are incorporated into the present application by reference.

The preferred platinum compound to be used not only as a platinum catalyst but also as a flame retardant additive is that disclosed in U.S. Pat. No. 3,775,452, Karstedt. Generally speaking, this type of platinum complex is formed by reacting chloroplatinic acid containing 6 moles of water of hydration with tetravinyltetramethylcyclosiloxane in the presence of sodium bicarbonate in an ethanol solution.

It has been found that the instant process is especially useful for removing platinum poisoning impurities from methyldichlorosilane such that when so purified by the instant process the methyldichlorosilane can easily enter a reaction with 3,3,3-trifluoropropene in the preparation of fluorosilicone polymers.

Methyldichlorosilane is purified by the instant process and then it is reacted with 3,3,3-trifluoropropene to produce methyl-3,3,3-trifluoropropyldichlorosilane. Such dichlorosilane is taken and then it is hydrolyzed to produce a mixture of linear low molecular weight fluoro-substituted silicone polymers and a mixture of fluoro-substituted cyclopolysiloxanes. By adding to this hydrolyzate anywhere up to 1% by weight of a strong alkali metal hydroxide, such as potassium hydroxide, and heating the mixture at temperatures above 180° C., the hydrolyzate is cracked and there is preferentially distilled and separated the fluoro-substituted cyclotrisiloxanes. In an alternative procedure, the cyclotrisiloxane is not distilled and separated out but the mixture is heated at elevated temperatures so as to preferentially form fluoro-substituted cyclotetrasiloxanes. By then taking such cyclotrisiloxanes or cyclotetrasiloxanes and reacting them at certain specified temperatures with an alkali metal hydroxide catalyst in the case of the cyclotrisiloxane and alkali metal silanolate in the case of the cyclotetrasiloxane, there may be obtained linear fluoro-substituted polysiloxane polymers of high viscosity. The fluoro-substituted polysiloxane polymers have a viscosity of anywhere from 1000 to 200,000,000 centipoise at 25° C. To these polymers there may be added various fillers and other additives and the materials cured with a peroxide catalyst to yield a fluoro silicone elastomer, which has exceptional solvent resistance to hydrocarbon fuels.

By the foregoing process there may also be obtained olefinic-containing or vinyl-containing fluoro-substituted polysiloxane polymers of a viscosity varying anywhere from 1000 to 200,000,000 centipoise at 25° C., which can enter the SiH-olefin platinum catalyzed reactions to produce fluoro-substituted silicone elastomers at room temperature. An example of such room temperature vulcanizable fluorosilicone elastomeric compositions is, for instance, to be found in the U.S. Patent of Jeram, U.S. Pat. No. 4,041,010, which is hereby incorporated by reference.

The examples given below are given for the purpose of illustrating the present invention. They are not given for any purpose of setting the limits or defining the scope of the instant disclosure and claims. All parts in the examples are by grams.

EXAMPLE 1

Methyldichlorosilane which had been purified by redistillation was found to have the following analysis by gas chromatography:

| Silanes | Percent | Hydrocarbons | Percent |
| --- | --- | --- | --- |
| $MeH_2SiCl$ | 0.00 | $CH_3CH(CH_3)CH_2CH_3$ | 0.00 |

-continued

| Silanes | Percent | Hydrocarbons | Percent |
|---|---|---|---|
| $Me_4Si$ | 0.00 | $CH_3CH_2C(CH_3)CH_2$ | 0.00 |
| $HSiCl_3$ | 0.00 | $CH_3CHC(CH_3)CH_3$ | 0.00 |
| $Me_2HSiCl$ | 0.00 | $CH_3CH_2C(CH_3)_2CH_3$ | 0.03 |
| $MeHSiCl_2$ | 99.97 | $CH_3CH(CH_3)CH_2CH_2CH_3$ plus | |
| | | $CH_3CH(CH_3)CH(CH_3)CH_3$ | 0.00 |
| $Me_3SiCl$ | 0.00 | $CH_3CH_2CH(CH_3)CH_2CH_3$ | 0.00 |
| $MeSiCl_3$ | 0.00 | Others | 0.00 |
| $Me_2SiCl_2$ | 0.00 | | |
| Others | 0.00 | | |
| Total | 99.97 | Total | 0.03 |

This $MeHSiCl_2$ (115 g., 1 mole) was placed in the stainless steel bottle of a Parr Hydrogenation Apparatus and 0.30 ml. of the platinum catalyst containing 5.0 percent platinum was added. This mixture was heated to above 50° C. and $F_3CCH=CH_2$ was pressured into the bottle to give above 10 lbs. total gauge pressure. The bottle was shaken mechanically but no drop in pressure was observed, indicating the absence of a reaction. Shaking was continued for 1 hour but the reaction failed to initiate. The bottle was then allowed to cool and depressured by venting the $F_3CCH=CH_2$. An additional 0.30 ml. of the platinum catalyst containing 5.0 percent platinum was added and the reaction was again attempted but failed to initiate in 1 hour.

EXAMPLE 2

A glass column fitted with a stopcock at the bottom was filled with Calgon Pittsburg Cal carbon (12 × 40 mesh) which had previously been activated by heating at 200° C. for two days. The carbon bed measured 20 cm. long by 2 cm. diameter — and contained 55 g. of carbon. Methyldichlorosilane (see analysis in Example 1) was slowly fed to the column which heated from the initial adsorbtion exotherm. When the column had cooled to room temperature, $MeHSiCl_2$ was drawn off the bottom and make-up $MeHSiCl_2$ was added at the top. The rate of take-off was about 1.6 g/min. Two fractions were collected.
Cut I: 90 g.
Cut II: 246 g.

In Cut I, there was 96.54% of methyldichlorosilane, 3.3% of other silane impurities, and 0.03% of organic impurities.

In Cut II, there was 99.69% of methyldichlorosilane, 0.28% of other silane impurities and 0.02% of organic impurities.

Both Cut I and Cut II of this $MeHSiCl_2$ were tested in the hydrosilation reaction as in Example 1 using the same proportions of Karstedt's platinum catalyst and the same $CF_3CH=CH_2$. Both reactions initiated immediately and ran as fast as the $CF_3CH=CH_2$ could be fed to the apparatus.

The product, $CF_3CH_2CH_2Si(Me)Cl_2$, appeared normal by gas chromatography analysis.

EXAMPLE 3

Union Carbide Corporation 13 × molecular sieves were activated by heating at 200° C. for 2 days. A glass column fitted with a bottom stopcock was half-filled with the $MeHSiCl_2$ of Example 1. The activated sieves were then slowly added to the column (adsorption exotherm) until a bed 56 cm × 2.5 cm (154g of sieves) had been built. When the column had cooled to room temperature, $MeHSiCl_2$ was drawn off the bottom at about 3.5 ml. per minute while adding fresh untreated $MeHSiCl_2$ at the top. Four fractions were collected.
Cut 1: 180 g.
Cut 2: 222 g.
Cut 3: 672 g.
Cut 4: 183 g.
Analysis of Cuts 1, 2 and 4 follow:

| Component Silanes | Cut 1 | Cut 2 | Cut 4 |
|---|---|---|---|
| $MeH_2SiCl$ | 0.00 | 0.00 | 0.00 |
| $Me_4Si$ | 0.00 | 0.00 | 0.00 |
| $HSiCl_3$ | 0.00 | 0.00 | 0.00 |
| $Me_2HSiCl$ | 0.00 | 0.00 | 0.00 |
| $MeHSiCl_2$ | 93.68 | 100.00 | 98.62 |
| $SiCl_4$ | 0.00 | 0.00 | 0.00 |
| $Me_3SiCl$ | 0.00 | 0.00 | 0.00 |
| $MeSiCl_3$ | 0.00 | 0.00 | 0.00 |
| $Me_2SiCl_2$ | 0.00 | 0.00 | 0.00 |
| Others | 3.32 | 0.00 | 0.00 |
| Residue | 2.96 | 0.00 | 1.34 |
| Hydrocarbons | Cut 1 | Cut 2 | Cut 4 |
| $CH_3CH(CH_3)CH_2CH_3$ | 0.00 | 0.00 | 0.01 |
| $CH_3CH_2C(CH_3)CH_2$ | 0.00 | 0.00 | 0.00 |
| $CH_3CHC(CH_3)CH_3$ | 0.00 | 0.00 | 0.03 |
| $CH_3CH_2C(CH_3)_2CH_3$ | 0.01 | 0.00 | 0.00 |
| $CH_3CH(CH_3)CH_2CH_2CH_3$ plus | | | |
| $CH_3CH(CH_3)CH(CH_3)CH_3$ | 0.00 | 0.00 | 0.00 |
| $CH_3CH_2CH(CH_3)CH_2CH_3$ | 0.00 | 0.00 | 0.00 |
| Others | 0.03 | 0.00 | 0.00 |

Cut 1 was subjected to the same hydrosilation reaction as in Example 1 but no reaction was observed with it.

Cut 2 and 4 were reacted with $CF_3CH=CH_2$ as in Example 2.

Reactions identical with Example 2 were observed for these fractions indicating the high reactivity of the sieve-treated $MeHSiCl_2$.

EXAMPLE 4

To a steel vessel 15 inches in inside diameter, 450 pounds of adsorbent (13 × molecular sieves, size 8 × 12 mesh, manufactured by Union Carbide Corporation) were charged. The height of the bed was 8.5 feet. The vessel was equipped with an outside jacket for either heating with steam or cooling with water. The bed of adsorbent was then dried by heating with 146 pounds per square inch gauge steam passing through the jacket and with a purge of nitrogen passing down through the bed of adsorbent at a rate of 2.5 standard cubic feet per minute overnight. The bed of adsorbent was then cooled to room temperature by passing cooling water through the jacket while continuing the nitrogen purge down through the bed.

Methyldichlorosilane which had been purified by redistillation and which had been tested for reactivity for the platinum-catalyzed addition of 3,3,3-trifluoropropene, as described in Example 1 and found to be non-reactive, was pumped upward through the bed of adsorbent at various feed rates and cuts of the effluent from the top of the bed were taken as shown in the following table. During Cut 1 cooling water was passed through the jacket of the vessel to remove the heat of adsorption evolved while the bed was being initially filled and wetted with the feed material.

| Cut | Feed Rate Gals./hr. | Mass Velocity lbs/hr./ft² | Nominal Residence Time, hrs. | Pounds of Product in Cut | Total lbs. of Product from bed |
|---|---|---|---|---|---|
| 1 | 28 | 210.8 | 2.80 | 2300 | 2300 |
| 2 | 19.7 | 148.4 | 3.97 | 4600 | 6900 |
| 3 | 20.5 | 154.5 | 3.82 | 4650 | 11550 |
| 4 | 10.3 | 77.6 | 7.60 | 2300 | 13850 |
| 5 | 24.2 | 182.3 | 3.24 | 2330 | 16180 |
| 6 | 24 | 180.8 | 3.26 | 3460 | 19640 |
| 7 | 48 | 361.7 | 1.63 | 3460 | 23100 |
| 8 | 30 | 226 | 2.61 | 1850 | 24950 |
| 9 | 42 | 316.4 | 1.86 | 1850 | 26800 |
| 10 | 50 | 376.7 | 1.56 | 3475 | 30275 |
| 11 | 60 | 452.1 | 1.31 | 3475 | 33750 |

Each of the cuts were tested for reactivity for the platinum catalyzed addition of 3,3,3-trifluoropropene as described in Example 1 using the same proportion of Karstedt's platinum catalyst and the same $CF_3CH=CH_2$. For each cut when tested, reaction initiated immediately and ran as fast as the $CF_3CH=CH_2$ could be fed to the apparatus.

The product, $CF_3CH_2CH_2Si(Me)Cl_2$ appeared normal by gas chromatography analysis.

Through cut 11, 33 750 pounds of purified product was collected which corresponds to 75 pounds of purified product per pound of adsorbent.

We claim:

1. A process for the purification of hydrogen-containing silanes and siloxanes comprising (1) contacting hydrogen-containing silanes and siloxanes having no aromatic substituent groups with an adsorbent bed comprising an adsorbent material selected from the class consisting of charcoal, and molecular sieves so as to remove therefrom all impurities which would poison a platinum catalyst, and (2) removing the purified silanes and siloxanes from the adsorbent bed.

2. The process of claim 1 wherein said hydrogen-containing silanes having no aromatic substituent groups are selected from the class consisting of $CH_3(H)SiCl_2$, $HSiCl_3$, $(CH_3)_2HSiCl$ and $H_2SiCl_2$.

3. The process of claim 1 further comprising contacting the said adsorbent bed with a first volume of the hydrogen-containing silane and siloxane until the adsorbent bed is thoroughly wetted; waiting until the adsorbent bed has reached room temperature; segregating said first volume; passing additional volumes of the hydrogen-containing silane and siloxane through the adsorbent bed and collecting the purified hydrogen silanes and siloxanes.

4. The process of claim 3 wherein the segregated first volume of hydrogen-containing silanes and siloxanes is recycled through said adsorbent bed.

5. The process of claim 1 wherein the adsorbent bed is formed from molecular sieves having a size in the range varying from ⅛ of an inch to 125 microns.

6. The process of claim 1 wherein the adsorbent bed comprises a form of charcoal which is activated carbon.

7. The process of claim 6 wherein the activated carbon has a size varying from one quarter of an inch to 3-4 microns.

8. The process of claim 1 wherein the adsorption process is carried out at a temperature in the range of 0° to 35° C.

9. The process of claim 8 wherein the adsorption process is carried out at room temperature.

10. The process of claim 1 wherein the hydrogen-containing silanes and siloxanes are doubly distilled so as to be purified before said silanes and siloxanes are passed into contact with said adsorbent bed.

11. The process of claim 1 wherein the hydrogen-containing silanes and siloxanes have a residence time in said adsorbent bed ranging from 0.5 to 10 hours.

12. The process of claim 11 wherein the hydrogen-containing silanes and siloxanes have a residence time in said adsorbent bed varying from 1 to 4 hours.

13. The process of claim 1 wherein in said process sufficient hydrogen-containing silanes and siloxanes are passed through said adsorbent bed such that there is at least 75 pounds of said hydrogen-containing silanes and siloxanes purified per pound of adsorbent material before said bed has to be replaced.

14. The process of claim 13 wherein in said process sufficient hydrogen-containing silanes and siloxanes are passed through said adsorbent bed such that from 75 to 500 pounds of said hydrogen-containing silanes and siloxanes are purified per pound of adsorbent material before said bed has to be replaced.

15. The process of claim 14 wherein said adsorbent bed is discarded after it has absorbed the maximum amount of impurities.

16. The process of claim 1 wherein said adsorbent bed is placed in a column.

17. The process of claim 1 wherein said hydrogen-containing silanes and siloxanes are passed through said adsorbent bed at a rate varying from 5 to 800 pounds per hour, per square foot of adsorbent bed cross-sectional area.

18. The process of claim 4 wherein the segregation of said first volume of hydrogen-containing silanes, the passing of additional volumes of hydrogen-containing silanes and siloxanes through said adsorbent bed and the recycling of said segregated silanes and siloxanes are carried out in a continuous manner.

19. The process of claim 18 wherein after the adsorbent bed is saturated with impurities the stream of hydrogen-containing silanes and siloxanes is passed to a second bed which has been wetted with silanes and siloxanes previously such that the purification of the hydrogen-containing silanes and siloxanes is continuously maintained.

20. The process of claim 1 such that after said silane is purified, which is methyldichlorosilane, it will react immediately with 3,3,3-trifluoropropene in the presence of a platinum catalyst.

21. The process of claim 1 such that after said silane is purified, which silane is dimethylchlorosilane, it will react immediately with vinylacetonitrile in the presence of a platinum catalyst.

22. The process of claim 1 such that after said siloxane, which is a polymethylhydrogensiloxane, is purified it will react immediately with an olefinic compound selected from the class consisting of a methyl styrene and hexene in the presence of a platinum catalyst.

23. A process for the purification of olefinic silanes or siloxanes comprising (1) contacting said olefinic silanes and siloxanes having no aromatic substituent groups with an adsorbent bed comprising an adsorbent material selected from the class consisting of charcoal, and molecular sieves so as to remove therefrom all impurities which would poison a platinum catalyst and (2) removing the purified silanes and siloxanes from the adsorbent bed.

24. A process for the continuous purification of hydrogen-containing silanes comprising (1) contacting said adsorbent bed with a first volume of the hydrogen-containing silane which is selected from the class consisting of $CH_3(H)SiCl_2$, $HSiCl_3$, $(CH_3)_2HSiCl_3$, and $H_2SiCl_2$ until the bed is thoroughly wetted; wherein the adsorbent bed is formed from molecular sieves having a size varying from ⅛ of an inch to 125 microns, (2) waiting until the adsorbent bed has reached room temperature, (3) segregating said first volume of silanes, (4) continuously passing additional volumes of the hydrogen-containing silanes through said adsorbent bed so as to remove all impurities therefrom which would poison a platinum catalyst, (5) removing the purified hydrogen-containing silanes, (6) recycling said segregated first volume of hydrogen-containing silanes through said adsorbent bed so as to purify them, (7) discarding said adsorbent bed when it is saturated with impurities, and (8) continuously passing said hydrogen-containing silanes through a new adsorbent bed which has already been wetted with silanes so as to continuously remove purified hydrogen-containing silanes wherein the adsorption process is carried out at a temperature in the range of 0° to 35° C., wherein said hydrogen-containing silanes and siloxanes have a residence time in said adsorbent bed varying from 0.5 to 10 hours, wherein from 75 to 500 pounds of such hydrogen-containing silanes are purified per pound of adsorbent material in said adsorbent bed before said adsorbent material has to be replaced and wherein said hydrogen-containing silanes are passed through said bed at a rate varying from 5 to 800 pounds per hour, per square foot of adsorbent bed cross-sectional area.

* * * * *